(12) United States Patent
Schultz

(10) Patent No.: US 8,236,340 B2
(45) Date of Patent: Aug. 7, 2012

(54) DRUG FORMULATIONS FOR COATING MEDICAL DEVICES

(75) Inventor: Robert K Schultz, Poway, CA (US)

(73) Assignee: REVA Medical, Inc., San Diego, CA (US)

( * ) Notice: Subject to any disclaimer, the term of this patent is extended or adjusted under 35 U.S.C. 154(b) by 1093 days.

(21) Appl. No.: 12/136,576

(22) Filed: Jun. 10, 2008

(65) Prior Publication Data

US 2008/0274159 A1 Nov. 6, 2008

Related U.S. Application Data

(62) Division of application No. 10/773,756, filed on Feb. 6, 2004, now abandoned.

(60) Provisional application No. 60/446,318, filed on Feb. 7, 2003.

(51) Int. Cl.
*A61F 2/02* (2006.01)

(52) U.S. Cl. ........................................................ 424/423

(58) Field of Classification Search ........................ None
See application file for complete search history.

(56) References Cited

U.S. PATENT DOCUMENTS 5,945,409 A 8/1999 Crandall

FOREIGN PATENT DOCUMENTS

WO WO01/24866 4/2001

OTHER PUBLICATIONS

Charles et al., 2000 "Ceramide-coasted balloon catheters limit neointimal hyperplasia after stretch injury in carotid arteries." Circ. Res. 87:282-288.
"Lecithin", Hawley's Condensed Chemical Dictionary, 14$^{th}$ Edition, 2002.

*Primary Examiner* — Carlos Azpuru
(74) *Attorney, Agent, or Firm* — Knobbe Martens Olson & Bear LLP

(57) ABSTRACT

The present invention relates to oil-based formulations of hydrophobic drugs for the uniform coating of medical devices such as vascular stents and balloons. Another aspect of the present invention is an intravascular medical device having an oil-based coating suitable for delivering a water-insoluble drug, comprising one or more of an anti-oxidant, an anti-inflammatory and an anti-restenotic agent.

14 Claims, 1 Drawing Sheet

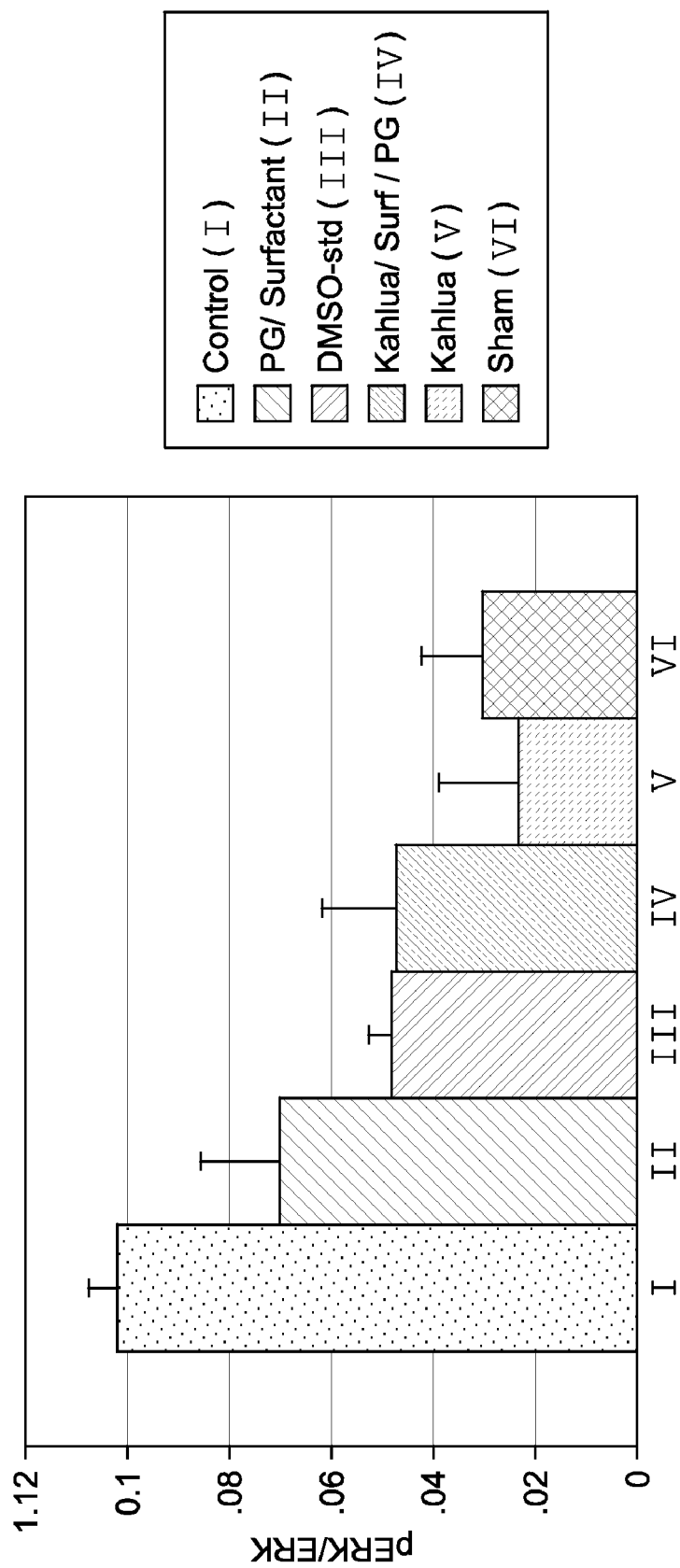

DRUG FORMULATIONS FOR COATING MEDICAL DEVICES

CROSS-REFERENCE TO RELATED APPLICATIONS

This application is a divisional of U.S. patent application Ser. No. 10/773,756, filed on Feb. 6, 2004 and entitled "Drug Formulations for Coating Medical Devices," which claims the benefit of U.S. Provisional Patent Application No. 60/446,318, filed on Feb. 7, 2003 and also entitled "Drug Formulations for Coating Medical Devices."

BACKGROUND OF THE INVENTION

1. Field of the Invention

The present invention is related to the delivery of drugs from implantable medical devices. More specifically, the present invention relates to formulations of hydrophobic anti-oxidant, anti-inflammatory and anti-restenotic agents and vascular stents and balloons having an oil-based coating suitable for delivering anti-oxidant, anti-inflammatory and anti-restenotic agents.

2. Description of the Related Art

Over one million angioplasty procedures are performed annually with about 80% of these involving the placement of a metal stent. Although, both balloon angioplasty and stenting of clogged coronary arteries result in an immediate clearing of the obstruction and resumption of coronary blood flow, within six months 20-50% of the arteries require revascularization. The mechanism of restenosis has been found to be related to both mechanical stretch injury and remodeling of the artery wall due to smooth muscle cell proliferation into the lumen called neointimal hyperplasia (NIH). In both instances, the cause of the reduced artery flow is actually induced by balloon angioplasty and/or placement of the stent. Originally, balloon angioplasty by itself was responsible for stretch injury and recoil that lead to as much as 50% restenosis in susceptible patients. To counter the effects of recoil and prop the artery open further, the practice of deploying a metal stent was introduced and the values of restenosis have dropped to between 20-30% depending on the patient population.

Drugs such as rapamycin and paclitaxel have been demonstrated to reduce NIH and further reduce the rate of stenosis when coated on a metal stent. These drugs act to prevent smooth muscle cell (SMC) proliferation which is a direct consequence of the damage done to the internal elastica and the medial layers during the deployment of the balloon and/or stent. A new agent C6-ceramide (CERACOR™)—a water insoluble lipid, has also been demonstrated to inhibit SMC proliferation in both in vitro cell culture and in vivo animal studies (rabbit carotid model and pig coronary) (Charles et al. 2000 *Circ Res* 87:282-288). C6-ceramide has been shown to initiate activity within 15 minutes of application of a single dose from an angioplasty balloon.

Initial experiments with C6-ceramide coated on the balloon from a dimethylsulfoxide/ethanol solution revealed that the physical form of the drug changes with time. Initially, the deposited lipid form a translucent film, but within an hour or so the deposited material slowly transforms to a white crystallite appearance. The deposition uniformity as measured by microscopy is spotty across the balloon surface. After several days, the white powder continues to transform until it flakes off the balloon and is no longer believed to be in an available state. Decreased availability may be described as the dissolution/deaggregation time of the solid relative to deposition and diffusion within the artery, which prevents it from exerting its effect. Currently, to study the effect of C6-ceramide in animal models, the DMSO/ethanol formulation containing C6-ceramide is coated onto the balloon just prior to insertion into the artery. The role of the solvent is to keep the lipid material in an available film-like state sufficient for it to be rapidly deposited and absorbed quickly in the artery, where it is shown to exert an effect within 15 minutes. However, organic solvents, in which the drug is very soluble, tend to evaporate rapidly and the solvents may also penetrate and affect the balloon performance. Alternative solvents and formulations are needed that permit the drug to remain in a dissolved state yet remain physically stable without changing with time.

SUMMARY OF THE INVENTION

In one embodiment, the present invention relates to a formulation for coating a medical device with a hydrophobic restenosis-inhibiting agent. The formulation comprises the hydrophobic restenosis-inhibiting agent, a non-volatile oil-based solvent, and an amount of a volatile solvent sufficient to decrease the viscosity of the non-volatile oil-based solvent, such that the formulation is adapted to uniformly coat the medical device.

In a preferred embodiment of the coating formulation, the hydrophobic restenosis-inhibiting agent is C6-ceramide. In another preferred variation of the coating formulation, the non-volatile oil-based solvent comprises Vitamin E. Preferably, the volatile solvent comprises ethanol. In one particularly preferred embodiment, the pharmaceutical formulation, comprising C6-ceramide and Vitamin E.

In another aspect, the present invention relates to an implantable medical device comprising a surface adapted to contact a vessel wall, wherein the surface has a coating comprising a hydrophobic restenosis-inhibiting agent, and a non-volatile oil-based solvent in which said agent is dissolved. This device may be an intravascular balloon. In a variation, the device may be an intravascular stent. Preferably, the oil-based solvent comprises Vitamin E. More preferably, the device is coated with Vitamin E and C6-ceramide.

In another aspect, the present invention relates to a method for producing a drug-coated intravascular device. The method comprises the steps of producing a coating composition by mixing a drug composition comprising a water-insoluble restenosis inhibiting agent and an oil-based non-volatile solvent in a volatile solvent; coating the intravascular device with the coating composition; and causing the volatile solvent to evaporate. Preferably, the oil-based non-volatile solvent comprises Vitamin E, and the volatile solvent comprises ethanol. Preferably, the restenosis-inhibiting agent is C6-ceramide. In a further aspect, the present invention is the drug-coated intravascular device produced by the above method.

BRIEF DESCRIPTION OF THE DRAWINGS

FIG. 1 shows the results of screening of activity of several formulations in the rabbit carotid stretch injury model.

DETAILED DESCRIPTION OF THE PREFERRED EMBODIMENT

In one embodiment, the present invention is an oil-based formulation of hydrophobic anti-restenosis drugs for uniform coating of a medical implantable device such as a vascular balloon or a stent.

In another embodiment, the present invention is a method of coating of medical implantable devices such as vascular balloons and stents with water-insoluble drugs dissolved in an oil-based solvent.

In another embodiment, the present invention is a medical implantable device such as a vascular balloon or a stent coated with an oil-based formulation containing a water-insoluble drug.

For the purpose of this invention by a water-insoluble drug, or hydrophobic drug we mean a drug with a water solubility of less than about 1 mg/ml at room temperature and a log P, where P is the partition coefficient between octanol and water, of at least 1.5, preferably at least 2.

Three formulation approaches have shown significant promise for the delivery of rapidly acting water-insoluble drugs to the coronary arteries.

Formulation Approach 1: Propylene glycol+Surfactant.

Formulation Approach 2: Intravenously acceptable oils (cottonseed, peanut), Vitamin E.

Formulation approach 3: Propylene glycol+Surfactant+oil.

C6-ceramide was found to be sufficiently soluble and/or dispersible in all three formulation approaches when all components were first dissolved in a volatile solvent, such as ethanol. In all cases the drug was coated onto a balloon from an ethanol solution containing C6-ceramide and the other solvents in each formulation. Once the ethanol evaporated from the surface of the device, the drug was uniformly dispersed over the surface and dissolved within the non-volatile solvent (s). The ethanol was useful in that it decreased the viscosity of the oil/drug mixture thereby promoting uniform coating. It was found that although the oils, other than vitamin E, formed an emulsion with ethanol, the coating performance was adequate.

In all cases the C6-ceramide coated onto the angioplasty balloon in a formulation containing a non-volatile solvent appeared to maintain the drug in the dissolved state rather than forming a dispersed solid, as was the case for DMSO formulations. Maintaining the drug in the dissolved state uniformly coated over the surface of the balloon is desirable for improving uniformity of delivery to the artery wall.

Additional water-insoluble drugs may be used depending on their solubility and coating performance, including rapamycin, rapamycin analogs, ABT-578, everolimus, paclitaxel, dexamethasone and other lipid materials (e.g., other ceramides, dimethyl sphingosine, ether-linked diglycerides, ether-linked phosphatidic acids, and sphinganines, and other phospholipids). Indeed other compounds could be dispersed in the oil-based formulation of the present invention. Particularly in cases where, even if they had low solubility in the oil itself, sufficient drug could be dispersed either by using appropriate cosolvents and surfactants or by making a dispersed paste of the hydrophobic drug in the oil.

The following exemplary hydrophobic materials that may also be compatible with this oil dispersion approach include but are not limited to: steroids such as Dexamethasone, 17-beta-Estradiol; Rapamycin and analogues; Taxol (paclitaxel) and analogues; Actinomycin D; Prostaglandins (PGE1); Vitamin A; Probucol; Batimastat; Statins (HMG-CoA Reductase Inhibitors), particularly the water insoluble base forms that can be formulated as dispersions in the oil; Trapidil (and other anti-proliferative Growth Factor Inhibitors); and Cytochalasin B.

The devices which may be enhanced by coating with the formulations of the present invention include any intraluminal devices adapted for delivery to selected sites within the cardiovascular system. These include, for example, simple catheter/simple (one) balloon designs, dual balloon catheters, stents, microporous catheters infusion catheters, rotary atherectomy devices, ablation catheters, polymeric (e.g., polyacrylic acid) coated balloon designs, bioabsorbable coating designs, stent covers and perivascular matrices.

The device to be coated is preferably dipped in a vehicle including a volatile solvent (e.g., ethanol), a non-volatile oil-based solvent, and a hydrophobic drug. The actual coating process may be performed in a clean environment. If the device has a balloon, it is preferably expanded prior to coating. Once the volatile solvent evaporates from the surface of the device, the drug is uniformly dispersed over the surface of the device and dissolved or dispersed within the non-volatile solvent or carrier. Post-processing sterilization can be accomplished by any methods known in the art which do not negatively impact the drug activity, the quality of the coating and/or device itself. For example, the coated device can be subjected to radiation sterilization.

When coated onto a standard commercially available angioplasty balloon/delivery system, the oil-based formulations containing a water insoluble drug:

uniformly coat the surface of the expanded balloon;

the coated balloon can be deflated and re-wrapped to permit transport to the coronary artery lesion site with the smallest crossing profile;

when redeployed the oil-based C6-ceramide coating remains dispersed over the entire surface of the balloon;

little dissolution or removal of the drug from the surface occurs prior to inflation of the balloon in the artery;

the basis of drug transport remains transfer of drug from the surface of the balloon to the artery wall during inflation of the balloon. The amount of drug transferred is typically less than 25% of the total amount of drug available on the surface;

after inflation the balloon can be rewrapped and removed from the artery or redeployed elsewhere to another lesion site, little drug is lost during removal process; and the oil-based formulations provide for a lubricious coating to the balloon without using polymers or hydrogels.

When used to coat metal coronary stents the oil-based formulations permit:

uniform coating of the entire metal surface;

coating can be applied to both the stent and the delivery balloon at the same time;

unlike the balloon-coated option that is removed from the artery immediately after deployment, the coated stent remains in place and will slowly deliver the entire amount of drug to the artery wall. The dissolution rate of the oil-based hydrophobic drug system is compatible with sustained release delivery of the drug to the artery wall without a controlling polymer or hydrogel; and wound healing potential as vitamin E's antioxidant activity may augment the anti-restenotic activity of the drug and enhance wound healing at the site where the stent struts are embedded in the artery wall.

The current formulation approach applied to an angioplasty balloon demonstrates rapid pressure transfer delivery of a sufficient amount of water-insoluble materials to the artery wall using a non-polymer/hydrogel base consisting of oil capable of dispersing the drug. The formulation approach works to keep a lipid material in a very deliverable form without further solid-state changes that could lead to ineffective delivery. The delivery of the drug is largely based on contact of the balloon surface to the artery wall and the coating uniformity of the oil-based formulations is superior to other organic solvents. By increasing the coating uniformity the resultant deposition of the drug on the artery wall will be uniform as well as possibly improving the overall activity of the drug.

The formulation approach outlined here is applicable to both stents and balloons. For a stent, the viscosity and dissolution rate of the resulting oil/drug mixture is tunable based on the concentration of both oil and drug. Enhanced wound healing and anti-oxidant behavior likely will increase when the choice of the oil is vitamin E possibly leading to a synergistic effect of the drug/oil mixture. Other possible oils that can be used in the present invention include but are not limited to: fish oils (for example, EPA, eicosapentanenoic acid, and DHA, docosahexaenoic acid); vegetable oils (for example, cottonseed, corn, sassafras, sunflower oils), and Vitamin A. Various surfactants known in the art may be used in the present invention, for example, Polyoxyl 40 Stearate (Myrj 52), lecithin, Poloxamer, and the like.

The compatibility of the oil-based formulation approach to the delivery of many different classes of compounds permits the combination of anti-oxidant, anti-inflammatory and anti-restenotic agents into one delivery vehicle that could be an important weapon in the prevention of restenosis.

This invention is further illustrated by the following examples which should not be construed as limiting. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Study #1 pERK/ERK

C6-ceramide has been shown in vitro and in vivo to prevent the up-regulation of extracellular signal-regulated kinase (ERK) to its phosphorylated state (pERK) following balloon stretch injury. The lack of up-regulation in this kinase has been correlated to the prevention of restenosis in the rabbit carotid stretch injury model. Using the standard rabbit carotid stretch injury model the activity of oil-based/non-volatile formulations were screened. FIG. 1 shows the results of this screening. As can be seen with the 1% vitamin E (code name Kahlua) formulation, the effect on pERK following stretch injury was not significantly different from the sham control artery that did not receive any injury.

Study #2 Stenosis

In a parallel study a formulation containing 1% vitamin E, 0.5% propylene glycol, 0.05% Myrj 52 and 0.5% (w/w) C6-ceramide dissolved in ethanol was evaluated in the rabbit carotid balloon injury model. The same procedure was used as above except the endpoint of this study was 14 day histology to measure neointimal hyperplasia (NIH) as represented by the percentage decrease in the neointimal area of the injured artery (percent stenosis). Here, the oil-based formulation resulted in more than a 50% reduction of neointimal hyperplasia (index of stenosis).

In both experiments it was possible to achieve equal or better performance from the oil-based formulation approaches compared to the existing DMSO/C6-ceramide solvent-treated.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A medical device comprising a coating,
wherein the coating comprises i) a non-volatile oil-based solvent, ii) a hydrophobic therapeutic agent selected from the group consisting of rapamycin, rapamycin analogs, ABT-578, everolimus, paclitaxel, dexamethasone, ceramides, dimethyl sphingosine, ether-linked diglycerides, ether-linked phosphatidic acids, sphinganines, steroids, taxol, taxol analogs, actinomycin D, prostaglandins, vitamin A, probucol, Batimastat, Statins, Trapidil, and Cytochalasin B, and iii) an amount of volatile solvent sufficient to decrease the viscosity of the non-volatile oil-based solvent,
wherein the hydrophobic therapeutic agent is transferrable to a vessel upon contact therewith and is uniformly dispersed over the medical device within the non-volatile oil-based solvent.

2. The medical device of claim 1, wherein the medical device is an intravascular balloon.

3. The medical device of claim 1, wherein the medical device is an intravascular stent.

4. The medical device of claim 1, wherein the oil-based solvent comprises Vitamin E.

5. The medical device of claim 1, wherein the hydrophobic therapeutic agent is a restenosis-inhibiting agent.

6. The medical device of claim 5, wherein the restenosis-inhibiting agent is selected from rapamycin, paclitaxel, or their analogs.

7. The drug-coated intravascular device produced by a method comprising:
producing a coating composition by mixing a drug composition comprising a drug and an oil-based non-volatile solvent in a volatile solvent,
coating said intravascular device with said coating composition; and
causing said volatile solvent to evaporate.

8. The medical device of claim 1, wherein the medical device is an intravascular medical device.

9. The medical device of claim 1, wherein the medical device is an expandable medical device.

10. The medical device of claim 1, wherein the volatile solvent comprises ethanol or isopropanol.

11. The medical device of claim 1, wherein the dissolution rate of the hydrophobic therapeutic agent is compatible with sustained release delivery of the hydrophobic therapeutic agent to an artery wall.

12. The medical device of claim 1, wherein the coating comprises a base consisting of an oil capable of dispersing the hydrophobic therapeutic agent, so as to provide a lubricious surface to the medical device without using polymers or hydrogels.

13. The medical device of claim 12, wherein the coating base is a non-polymer base.

14. The medical device of claim 12, wherein the coating base is a non-hydrogel base.

* * * * *